United States Patent [19]

Gehlhaus et al.

[11] 4,450,276

[45] May 22, 1984

[54] PROCESS FOR THE PREPARATION OF D(+)-BIOTIN

[75] Inventors: Jürgen Gehlhaus, Port Chester, N.Y.; Claus P. Herz, Heidelberg, Fed. Rep. of Germany

[73] Assignee: Merck Patent Gesellschaft mit beschränkter Haftung, Darmstadt, Fed. Rep. of Germany

[21] Appl. No.: 386,134

[22] Filed: Jun. 7, 1982

[30] Foreign Application Priority Data

Jun. 6, 1981 [DE] Fed. Rep. of Germany ....... 3122562

[51] Int. Cl.³ ............................................ C07D 495/04
[52] U.S. Cl. .................................... 548/303; 549/435; 549/454
[58] Field of Search ......................................... 548/303

[56] References Cited

PUBLICATIONS

Vogel, F., et al., *Liebigs Ann. Chem.*, 1980, 1972–1977.

Primary Examiner—Richard A. Schwartz
Attorney, Agent, or Firm—Millen & White

[57] ABSTRACT

The stereospecific preparation of D(+)-biotin is improved by a synthetic route involving the conversion of 3,4-isopropylidene-D-arabinose in which the OH group in the 2-position is not protected, into an ester of 6,9-dihydroxy-7,8-isopropylidenedioxynona-2,4-dienoic acid, the latter then being catalytically hydrogenated and subsequently converted into D(+)-biotin in a manner known per se.

5 Claims, No Drawings

PROCESS FOR THE PREPARATION OF D(+)-BIOTIN

BACKGROUND OF THE INVENTION

The present invention relates to a new process for the stereospecific synthesis of D(+)-biotin.

Stereospecific syntheses of biotin starting from sugars of suitable configuration are known. Such a synthesis, starting from D-mannose, is described in Tetrahedron Letters No. 32, pages 2765–2766, 1975. An improved synthesis, starting from D-arabinose and continuing with the above-mentioned synthesis at the stage of the ester of 6,9-dihydroxy-7,8-isopropylidenedioxynonanoic acid is described in Liebig's Annalen der Chemie 1980, pages 1972–1977.

In the latter, the cyclic hemiacetal form of 3,4-isopropylidenearabinose is protected in the 2-position by a benzoyl group and reacted with a phosphorus ylide. Subsequent hydrogenation and cleavage of the protecting group leads to the above-mentioned ester of nonanoic acid, which can be converted to D(+)-biotin in a known manner.

However, even this improved synthesis is still not satisfactory, because a large number of reaction steps are necessary, which means that the overall yield is not very high.

SUMMARY OF THE INVENTION

Thus, it is an object of this invention to provide a stereospecific synthesis for D(+)-biotin, requiring fewer reaction steps and having an improved yield.

Upon further study of the specification and appended claims, further objects and advantages of this invention will become apparent to those skilled in the art.

These objects have been obtained by the finding that the protection of the OH group in the 2-position of the 3,4-isopropylidene-D-arabinose by a benzoyl group, which is reported as indispensible in Liebig's Annalen der Chimie, is, surprisingly, not necessary under suitable reaction conditions. As a result, two reaction steps can be eliminated and the overall yield raised.

Thus, the present invention relates to the process described above, wherein 3,4-isopropylidene-D-arabinose in which the OH group in position 2 is not protected, is converted into an ester of 6,9-dihydroxy-7,8-isopropylidenedioxynona-2,4-dienoic acid, which is catalytically hydrogenated and then converted to D(+)-biotin in a manner known per se.

DETAILED DISCUSSION

Since, in the synthesis described in Liebig's Annalen der Chemie, a loss of yield of nearly 50% occurs due to the attachment and cleavage of the protecting group, the main advantage of the process according to this invention, apart from the savings in time and capacity of apparatus, is above all the improvement of the overall yield of D(+)-biotin.

The 3,4-isopropylidenearabinose required as starting material can be prepared, for example, by the process described in the Journal of the American Chemical Society 79, page 165, 1957, which is incorporated by reference herein. The further conversion of the isopropylidenearabinose is carried out in accordance with the following scheme of reactions:

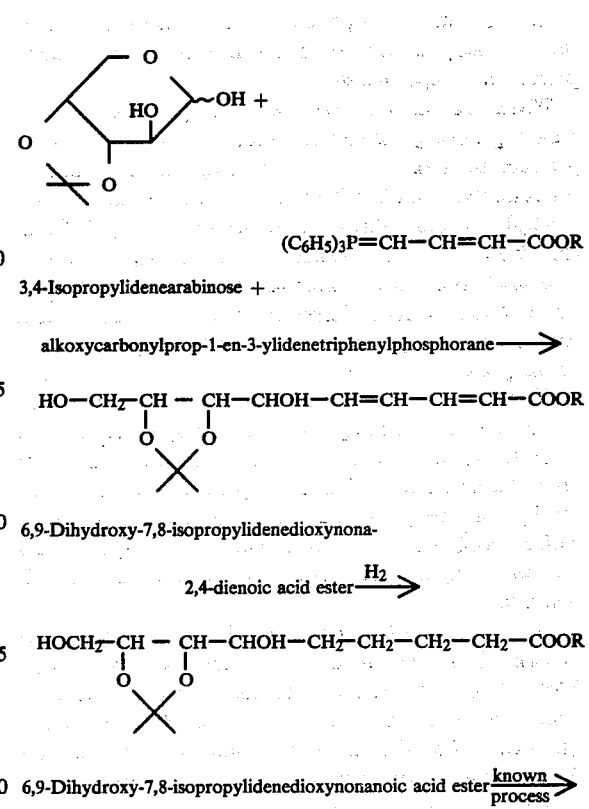

Suitable alkoxy groups in the phosphorane include, in particular, alkoxy groups of, for example, 1 to 12 C atoms; methoxy and ethoxy are preferred.

For the reaction of the isopropylidenearabinose with the phosphorane, the two components can be dissolved in a suitable solvent and stirred at a temperature of from room temperature to the boiling point of the solvent, preferably at about 25° to 100° C., for about 0.5 to 24 hours, preferably about 1 to 5 hours. In contrast to the known process, in which the phosphorane is employed in a threefold molar excess, in the process according to this invention approximately equimolar amounts are preferably employed. This is a further advantage of the process of this invention.

It is important that the solvent used be a polar, non-basic solvent. Suitable examples include aliphatic or cycloaliphatic ethers, for example tert-butyl methyl ether, ethylene glycol dimethyl ether, tetrahydrofuran or dioxane, and chlorinated hydrocarbons, for example, dichloromethane, dichloroethane or chloroform.

Surprisingly, it has been found decisive for the success of the reaction that it be conducted in a neutral to weakly acid medium. Apparently the reaction is so adversely affected by basic impurities, which can arise both in the preparation of the isopropylidenearabinose and in the preparation of the phosphorane, that no satisfactory results can be obtained. In contrast, if pure reagents are used or if basic impurities are neutralized by the addition of acidic reagents, the desired ester of nonadienoic acid is obtained in good yields.

Suitable such acidic agents include weak acids, for example benzoic acid, and also weakly or strongly acidic ion exchangers. These agents are added, if necessary, in such an amount as to produce a slightly acid reaction medium. As a rule, catalytic amounts of about 0.2 to 1% suffice. It is possible in each case to determine the necessary amount by a few indicative and routine preliminary experiments.

When the reaction with the phosphorane is completed, generally the solvent is removed and the desired product isolated from the remaining residue. Suitable processes for isolation have been found to include, for example, column chromatography on silica gel. From this, the ester of nonadienoic acid is obtained as a mixture of cis and trans isomers, as a rule in yields of about 50 to 70% of theory. These esters of nonadienoic acid are novel and represent a further advantageous aspect of the present invention.

These esters can be converted into the saturated esters of nonanoic acid by conventional hydrogenation, a single compound being produced from the mixture of cis and trans isomers. The hydrogenation can be carried out by customary methods—for example as a hydrogenation catalyzed by noble metals—at a slight excess pressure of hydrogen, in the solvents customary for this reaction.

The product obtained from the hydrogenation is known from Tetrahedron Letters No. 32, pages 2765–2766, 1975, whose disclosure is incorporated by reference herein; and can be converted into D(+)-biotin as described therein. A very advantageous process for the preparation of biotin is thus made available.

All details of this invention are conventional unless indicated otherwise herein and are disclosed, e.g., in the references cited above. Biotin or vitamin H is an important nutritional factor and can be used as an addition to diet.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

EXAMPLE 1

A solution of 38.0 g (0.2 mol) of 3,4-isopropylidene-D-arabinose and 74.8 g (0.2 mol) of ethoxycarbonyl-prop-1-en-3-ylidenetriphenylphosphorane in 500 ml of dimethoxyethane is stirred at room temperature in the presence of 2 g of an acid ion exchanger for 24 hours. After separating off the ion exchanger, the reaction mixture is freed from solvent and is chromatographed on silica gel with tert-butyl methyl ether as the mobile phase. 30.3 g (53% of theory) of ethyl 6,9-dihydroxy-7,8-isopropylidenedioxynona-2,4-dienoate is obtained.

Mass spectrum (70 eV): m/e=271 (3%, M+—CH$_3$), 156 (14%), 131 (38%), 97 (23%), 81 (24%), 59 (100%), 43 (35%), Infrared spectrum (film): 3460 (OH), 2980, 2930, 2890 (C—H), 1720 (C=O), 1640 (>C=C< trans), 1620 (>C=C< cis).

A solution of 28.6 g (0.1 mol) of the product obtained, in 250 ml of methanol, is mixed with 5 g of 5% Pd/MgO catalyst and hydrogenated at 20° C. and 1 bar pressure of hydrogen until no more hydrogen is absorbed. After filtering off the catalyst and removing the solvent, 29.0 g (100% of theory) of ethyl 6,9-diydroxy-7,8-isopropylidenedioxynonanoate remains.

EXAMPLE 2

A solution of 187 g of ethoxycarbonylprop-1-en-3-ylidenetriphenylphosphorane, 95 g of isopropylidenearabinose and 2 g of benzoic acid in one liter of dioxane is stirred at 60° to 70° C. for 3 hours. The residue obtained after removing the solvent in vacuo contains a mixture of cis and trans isomers of ethyl-6,9-dihydroxy-7,8-isopropylidenedioxynona-2,4-dienoate in a yield which corresponds to 62.8% of theory. The product can be hydrogenated to give the desired ethyl nonanoate as described in Example 1.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for preparing D(+)-biotin comprising reacting a 3,4-isopropylidine-D-arabinose with alkoxycarbonylprop-1-en-3-ylidenetriphenylphosphorane to give a product from which an ester of 6,9-dihydroxy-7,8-isopropylidenedioxynonanoic acid is obtained and converting the latter into D(+)-biotin, the improvement, comprising reacting 3,4-isopropylidene-D-arabinose in which the OH group in the 2-position is not protected, with said phosphorane essentially in the absence of alkaline components, to produce the corresponding ester of 6,9-dihydroxy-7,8-isopropylidenedioxynona-2,4-dienoic acid; catalytically hydrogenating the latter to form the corresponding ester of 6,9-dihydroxy-7,8-isopropylidenedioxynonanoic acid; and then converting the latter into D(+)-biotin.

2. A process of claim 1, wherein the reaction of the isopropylidenearabinose with the phosphorane is carried out in a neutral to slightly acid medium.

3. A process of claim 1, wherein the isopropylidenearabinose and the phosphorane are employed in approximately equimolar amounts.

4. A process of claim 1, wherein the reaction of the isopropylidenearabinose with the phosphorane is carried out in a polar, non-basic solvent at a temperature from room temperature up to the boiling point of the solvent for a period of 0.5 to 24 hours.

5. A process of claim 1, wherein the reaction of the isopropylidenearabinose with the phosphorane is carried out in the presence of a catalytic amount of a weak organic acid.

* * * * *